United States Patent [19]

Melville et al.

[11] Patent Number: 4,652,691

[45] Date of Patent: Mar. 24, 1987

[54] SELECTIVE ETHYLATION OF XYLENE WITH A METAL-MODIFIED, CRYSTALLINE BOROSILICATE MOLECULAR SIEVE

[75] Inventors: Judith B. Melville, Downers Grove; Richard E. Desimone, Lisle, both of Ill.

[73] Assignee: Amoco Corporation, Chicago, Ill.

[21] Appl. No.: 842,222

[22] Filed: Mar. 21, 1986

[51] Int. Cl.$^4$ .............................................. C07C 2/68
[52] U.S. Cl. .................................................... 585/467
[58] Field of Search ......................................... 585/467

[56] References Cited

U.S. PATENT DOCUMENTS 4,292,457  9/1981  Klotz .................................... 585/467

Primary Examiner—Curtis R. Davis
Attorney, Agent, or Firm—Reed F. Riley; William T. McClain; William H. Magidson

[57] ABSTRACT

Described is a process for selectively converting xylene in the gas phase with an ethylating agent under hydrocarbon conversion conditions to a highly pure 3,4-dimethylethylbenzene product in the presence of a catalyst composition comprising a metal-ion-modified, crystalline borosilicate molecular sieve in which the metal is intimately associated with the framework silica lattice, composited in an inorganic matrix.

12 Claims, No Drawings

SELECTIVE ETHYLATION OF XYLENE WITH A METAL-MODIFIED, CRYSTALLINE BOROSILICATE MOLECULAR SIEVE

BACKGROUND OF THE INVENTION

This invention relates to the selective gas phase ethylation of xylene to form a highly isomerically-pure dimethylethylbenzene product and to the use of catalyst compositions comprising metal-modified, crystalline borosilicate molecular sieves, incorporated into an inorganic matrix, for carrying out such selective ethylation. More particularly, this invention relates to the selective gas phase conversion of xylene to highly isomerically pure 3,4-dimethylethylbenzene by contacting xylene, pure or in a mixture, with an ethylating agent under hydrocarbon conversion conditions in the presence of a catalyst composition comprising a metal-ion-modified, crystalline borosilicate molecular sieve incorporated in an inorganic matrix in which the metal ion is intimately associated with the silica framework lattice. The process offers a simple route from xylene to a highly isomerically-pure 3,4-dimethylethylbenzene product having reduced isomer purification problems.

Catalyst compositions, generally useful for hydrocarbon conversion, based upon AMS-1B crystalline borosilicate molecular sieves have been described in U.S. Pat. Nos. 4,268,420, 4,269,813, 4,285,919, and published European Application No. 68796, all of which are incorporated herein by reference.

In U.K. Pat. No. 2,024,790B, catalyst compositions containing high specific surface area crystalline silica based materials modified by boron, which have been impregnated by Pt, Pd, Ni, Co, W, Cu, and Zn, are taught, which materials have catalytic usefulness in, inter alia, the alkylation of toluene with methanol. European Pat. No. 38682 teaches methanol-to-synthesis-gas conversion catalysts comprising a crystalline silica modified by inclusion of cobalt in the crystal lattice in place of a proportion of the silicon atoms. The catalyst is prepared by mixing in water or alcohol a source of silicon, a source of cobalt, a nitrogenous base such as a quaternary ammonium compound and, optionally, a mineralizing agent, and/or an inorganic base like sodium hydroxide. Also, European Pat. No. 63436 describes a methanol or olefin conversion catalyst of general formula 0–9 $M_2O$:a$Y_2O_3$:at least 100$XO_2$:0–35$H_2O$, where M is a monovalent cation or 1/n of a cation of valency n, a is from 0–9, X is silicon and Y can be one or more of aluminum, iron, chromium, vanadium, molybdenum, arsenic, antimony, manganese, gallium, or boron.

Selective production of 3,4-dimethylethylbenzene by alkylation of xylene over zeolite catalysts having a silica-to-alumina ratio of at least about 12 and a Constraint Index of greater than 2 and up to about 12 is taught in European Patent Application No. 0021600. The class of zeolites is exemplified by ZSM-5, ZSM-11, ZSM-23, and ZSM-35.

Catalyst compositions made using crystalline borosilicate molecular sieves have shown a great utility for hydrocarbon conversion reactions such as aromatic isomerization and alkylation reactions. While excellent for many purposes, it is desirable to fine-tune the borosilicate family of catalysts to perform more selectively in a particular type of hydrocarbon conversion reaction. Now it has been found that by incorporating a small amount of metal ion in the formation of a HAMS-1B molecular sieve, crystalline borosilicate-based molecular sieves, metalloborosilicates, can be produced which are very selective for producing the 3,4-dimethylethylbenzene isomer during the gas phase ethylation of a xylene alone or in a mixture.

SUMMARY OF THE INVENTORY

Described herein is a process comprising contacting xylene and an ethylating agent under hydrocarbon conversion conditions to selectively form 3,4-dimethylethylbenzene with a catalyst composition comprising a crystalline metalloborosilicate molecular sieve containing between about 0.1 weight percent and about 6 weight percent of metal ion selected from the group consisting of manganese, cobalt, nickel, copper, zinc, and ytterbium ions, said sieve made by crystallization from an aqueous solution containing ammonia or an organic base, an organic templating material, a metal ion-affording compound selected from soluble compounds of said metal ion, and sources of an oxide of silicon and boron and providing an X-ray pattern comprising the X-ray diffraction lines and assigned strengths to be found in Table A below.

These metalloborosilicates are made in such a way that the metal ion content of the sieve, while small, is incorporated differently in the crystalline lattice than metal ion-containing sieves made by ion exchange or impregnation processes. It is believed that the metal ion may be incorporated in the silica lattice of the crystalline metalloborosilicate sieve.

DETAILED DESCRIPTION OF THE INVENTION

Ethylation of xylene in the presence of the catalyst compositions according to this invention is effected by contact of xylene with an ethylating agent, preferably in the gas phase, at a temperature between about 200° and about 600° C. and preferably between about 250° and about 400° C. The reaction generally takes place at atmospheric pressure, but the pressure may be within the approximate range of about 1 atmosphere to about 2000 psig. The molar ratio of xylene to ethylating agent employed is within the approximate range of about 0.5 to about 50, more preferably about 2 to about 20. Reaction is suitably accomplished utilizing a weight hourly space velocity of between about 0.1 and about 100 and preferably between about 0.5 and about 50. The reaction product consisting primarily of the 3,4-dimethylethylbenzene isomer together with comparatively smaller amounts of other isomers may be separated from the other isomers and any unconverted feed materials by any suitable means such as fractionation.

Alkylating agents useful in this invention are ethylene and ethanol and more preferably ethylene is the alkylating agent of choice.

The xylene feed to the instant process can be a single isomer such as ortho-, meta-, or paraxylene or a mixture of such isomers. The feed can be either pure xylene or xylenes, or a xylene or xylenes in mixture with other materials such as ethylbenzene. Too much of an impurity which is ethylatable, however, wastes ethylation agent and should be pre-separated.

The crystalline metalloborosilicate molecular sieves of this invention are characterized by the representative X-ray pattern listed in Table A below and by the composition formula:

$$xM_{2/n}O:B_2O_3:ySiO_2:zH_2O$$

wherein M is hydrogen and one cation selected from the group manganese, cobalt, nickel, copper, zinc, and ytterbium, n is the valence of the cation, x is between about 2 and about 8 except for Yb where it is between about 0.2 and 0.8, y is between about 25 and about 600, and z is between 0 and about 160.

TABLE A

| Interplanar Spacing (1) d, Å | Assigned Strength | Interplanar Spacing (1) d, Å | Assigned Strength |
|---|---|---|---|
| 11.18 ± 0.20 | VS | 3.84 ± 0.10 | MS |
| 10.03 ± 0.20 | MS | 3.81 ± 0.10 | M |
| 9.75 ± 0.20 | W | 3.74 ± 0.10 | W |
| 6.35 ± 0.20 | W | 3.71 ± 0.10 | M |
| 5.98 ± 0.15 | W | 3.63 ± 0.10 | W |

(1) Copper K alpha radiation
(2) VW = very weak; W = weak; M = medium; MS = medium strong; VS = very strong It is believed that the small metal ion content of the sieves is at least in part incorporated in the silica lattice. Various attempts to remove the metal ion from the metalloborosilicate sieves by exhaustive exchange with sodium, ammonium, and hydrogen ions, although in some cases removing a small amount of metal ion, leaves a definite, residual, nonexchangeable metal percentage, maybe incorporated in the silica lattice.

The metalloborosilicate molecular sieve useful in this invention can be prepared by crystallizing an aqueous mixture, at a controlled pH, of a metal ion-affording compound, sources of an oxide of boron and an oxide of silicon, and an organic template compound.

Typically, the mol ratios of the various reactants can be varied to produce the crystalline metalloborosilicates of this invention. Specifically, the mol ratios of the initial reactant concentrations are indicated below:

| | Broad | Preferred | Most Preferred |
|---|---|---|---|
| $SiO_2/B_2O_3$ | 5–400 | 10–150 | 10–80 |
| $SiO_2/MO$ | 4–200 | 10–150 | 20–100 |
| Base/$SiO_2$ | 0.5–5 | 0.05–1 | 0.1–0.5 |
| $H_2O/SiO_2$ | 5–80 | 10–50 | 20–40 |
| Template/$SiO_2$ | 0–1 | 0.01–0.2 | 0.02–0.1 |

By regulation of the quantity of metal ion (represented as MO) and the quantity of boron (represented by $B_2O_3$) in the reaction mixture, it is possible to vary the $SiO_2/MO$ and the $SiO_2/B_2O_3$ molar ratios in the final product. In general it is desirable to have the metal ion content of the metalloborosilicate sieve of this invention between about 0.1 and about 6 percent by weight of metal ion. More preferably, the amount of metal ion should be between about 0.5 and about 4 weight percent metal ion. Too much metal ion in the reaction mixture can reduce the sieve crystallinity which can reduce the catalytic usefulness of the sieve.

The metal ion is selected from the group consisting of manganese, cobalt, nickel, copper, zinc, and ytterbium ions and more preferably from the group consisting of manganese, cobalt, nickel, and zinc ions. It is conveniently introduced into the molecular sieve synthesis mixture as a soluble metal salt such as the metal nitrate, acetate, chloride, etc.

More specifically, the material useful in the present invention is prepared by mixing a base, a boron oxide source, a metal ion-affording substance, an oxide of silicon, and an organic template compound in water (preferably distilled or deionized). The order of addition usually is not critical although a typical procedure is to dissolve the metal ion-affording substance in an excess of complexing organic or inorganic base such as ethylenediamine or ammonia in water, add the boric acid and then the template compound. Generally, the silicon oxide compound is added with stirring and the resulting slurry is transferred to a closed crystallization vessel for a suitable time. After crystallization, the resulting crystalline product can be filtered, washed with water, dried, and calcined.

During preparation, acidic conditions should be avoided. Advantageously, the pH of the reaction mixture falls within the range of about 8.0 to about 12.0, more preferably between about 9.0 and about 11.0, and most preferably between about 9.5 and 10.5.

Examples of oxides of silicon useful in this invention include silicic acid, sodium silicate, tetraalkyl silicates, and Ludox, a stabilized polymer of silicic acid manufactured by E. I. DuPont de Nemours & Co. Typically, the oxide of boron source is boric acid although equivalent species can be used such as sodium borate and other boron-containing compounds.

Organic templates useful in preparing the crystalline metalloborosilicate include alkylammonium cations or precursors thereof such as tetraalkylammonium compounds, especially tetra-n-propylammonium compounds. A useful organic template is tetra-n-propylammonium bromide. Diamines, such as hexamethylenediamine, can be used.

Organic bases useful in the process described herein are amines and substituted amines, particularly those compounds which are able to keep the metal ion in solution during formation of the sieve without tying up the metal ion so completely so as not to allow some of it to be incorporated in the sieve.

The crystalline metalloborosilicate molecular sieve can be prepared by crystallizing a mixture of sources for an oxide of silicon, an oxide of boron, an oxide of a metal, an alkylammonium compound and an organic base or ammonia such that the initial reactant molar ratios of water to silica range from about 5 to about 80, preferably from about 10 to about 50, and most preferably from about 20 to about 40. The silica-to-boron oxide molar ratio is preferably about 5 to about 400, more preferably about 10 to about 150 and most preferably about 10 to about 80. In addition, preferable molar ratios for initial reactant silica to oxide of metal range from about 4 to about 200, more preferably from about 10 to about 150, and most preferably from about 20 to about 100. The molar ratio of organic base or ammonia to silicon oxide should be about above about 0.05, typically below about 5, preferably between about 0.05 and about 1.0, and most preferably between about 0.1 and about 0.5. The molar ratio of alkylammonium compound, such as tetra-n-propylammonium bromide, to silicon oxide can range from 0 to about 1 or above, typically above about 0.005, preferably about 0.01 to about 0.2, and most preferably about 0.02 to about 0.1.

The resulting slurry is transferred to a closed crystallization vessel and reacted usually at a pressure at least the vapor pressure of water for a time sufficient to permit crystallization which usually is about 0.25 to about 20 days, typically is about one to about ten days, and preferably is about one to about seven days, at a temperature ranging from about 100° to about 250° C., preferably about 125° to about 200° C. The crystallizing material can be stirred or agitated as in a rocker bomb. Preferably, the crystallization temperature is maintained below the decomposition temperature of the organic template compound. Especially preferred conditions are crystallizing at about 150° C. for about three to about seven days. Samples of material can be removed during crystallization to check the degree of crystallization and determine the optimum crystallization time.

The crystalline material formed can be separated and recovered by well-known means such as filtration with aqueous washing. This material can be mildly dried for anywhere from a few hours to a few days at varying temperatures, typically about 50° to about 225° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination prodecure is necessary, if it is desired to remove this material from the final product. Typically, the mildly dried product is calcined at temperatures ranging from about 260° to about 850° C. and preferably from about 420° to about 600° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 165° C. for about 4 hours and is then calcined in air in a manner such that the temperature rise does not exceed 125° C. per hour until a temperature of about 540° C. is reached. Calcination at this temperature usually is continued for about 4 to 16 hour. The metalloborosilicate sieves thus made generally have a surface area greater than about 300 sq. meters per gram as measured by the BET procedure.

The metalloborosilicate sieve useful in this invention is admixed with or incorporated within various binders or matrix materials depending upon the intended process use. The crystalline metalloborosilicates are combined with active or inactive materials, synthetic or naturally-occurring zeolites, as well as inorganic or organic materials which would be useful for binding the metalloborosilicate. Well-known materials include silica, silica-alumina, alumina, magnesia, titania, zirconia, alumina sols, hydrated aluminas, clays such as bentonite or kaolin, or other binders well-known in the art. Typically, the metalloborosilicate is incorporated within a matrix material by blending with a sol of the matrix material and gelling the resulting mixture or slurrying the sieve with the matrix material and drying. Also, solid particles of the metalloborosilicate and matrix material can be physically admixed. Typically, such metalloborosilicate compositions can be pelletized or extruded into useful shapes. The crystalline metalloborosilicate content can vary anywhere from a few up to 100 wt.% of the total composition. Catalytic compositions can contain about 0.1 wt.% to about 100 wt.% crystalline metalloborosilicate material and preferably contain about 10 wt.% to about 95 wt.% of such material and most preferably contain about 20 wt.% to about 80 wt.% of such material.

More specifically, catalytic compositions comprising the crystalline metalloborosilicate material of this invention and a suitable matrix material are formed by adding a finely-divided crystalline metalloborosilicate sieve to an aqueous sol or gel of the matrix material, such as PHF Alumina made by American Cyanamid Co. The resulting mixture is thoroughly blended and gelled, typically by adding a material such as ammonium hydroxide. The resulting gel is dried below about 200° C., more preferably between about 100° and about 150° C. and calcined between about 350° and about 700° C. to form a catalyst composition in which the crystalline metalloborosilicate sieve is distributed throughout the matrix material.

Alternatively, the sieve and a suitable matrix material like alpha-alumina monohydrate such as Conoco Catapal SB Alumina can be slurried with a small amount of a dilute weak acid such as acetic acid, dried at a suitable temperature under about 200° C., preferably about 100° to about 150° C., and then calcined at between about 350° and about 700° C., more preferably between about 400° to about 650° C.

The catalyst compositions of this invention appear to be more selective for the ethylation of xylene when matrixed by the gel technique rather than the slurry technique, so the gel technique of making the catalyst compositions of this invention is preferred.

The catalyst compositions of this invention can be impregnated with a magnesium compound or a phosphorus compound or both, which can be accomplished using the catalyst composition in powder form or already in extrudate or pellet form.

To make the impregnated catalyst compositions, a composition comprising the acid form of the crystalline metalloborosilicate molecular sieve in an inorganic matrix is contacted with a phosphorus compound-containing solution. The resulting mass is then dried at temperatures up to about 150° C. removing in this step essentially all of the impregnation solvent. The resulting composition is then activated by calcination for 3 hours to about 24 hours at about 350° to about 650° C., more preferably about 4 hours to about 24 hours at about 400° to about 600° C. Care should be taken to avoid catalyst degradation during calcination.

The amount of phosphorus incorporated with the catalyst composition should be from about 1 to about 15 percent by weight, especially from about 2 to about 10 percent by weight, with the percents calculated as percent of the element.

Representative phosphorus compounds useful in the impregnation step include primary, secondary, or tertiary phosphines; tertiary phosphine oxides; primary and secondary phosphonic acids; esters of phosphonic acids; the dialkyl alkyl phosphonates; alkyl dialkyl phosphonates phosphinous acids, primary, second, and tertiary phosphites and esters thereof; alkyl dialkylphosphinites, dialkyl alkylphosphonites, their esters, phosphoric acid, phosphite esters such as triethylphosphite and ammonium phosphate salt. Preferred phosphorus-containing compounds include phosphoric acid, phosphite esters such as triethylphosphite, ammonium hydrogen phosphate and ammonium dihydrogen phosphate.

Magnesium compounds can be incorporated with the catalyst compositions in a manner similar to that employed with the phosphorus compounds above. Magnesium impregnation should result in about 4% to 20% by weight magnesium, preferably from about 8% to about 15% by weight magnesium, percent calculated as percent of the element. As with phosphorus, magnesium compound incorporation is effected by contacting the catalyst composition with the solution of an appropriate magnesium compound followed by drying and calcining to substantially convert impregnated magnesium compound to its oxide form. Preferred magnesium-containing compounds include most soluble magnesium salts, more preferably magnesium nitrate or acetate. Drying and calcination times and temperatures are generally the same as recited hereinbefore for drying the calcination of phosphorus-containing catalyst compositions.

The solutions of phosphorus or magnesium compounds used in impregnation may be made from polar or nonpolar solvents, including water and organic solvents generally. Solvents that are destructive of either the zeolite or matrix should be avoided. Water and alcohols are preferred solvents.

When both phosphorus and magnesium impregnation is used, the phosphorus compound and the magnesium compound are impregnated in the catalyst composition sequentially with phosphorus impregnation preceding magnesium impregnation.

The following Examples will serve to illustrate certain embodiments of the hereindisclosed invention. These Examples should not, however, be construed as limiting the scope of the novel invention as there are many variations which may be made thereon without departing from the spirit of the disclosed invention, as those of skill in the art will recognize.

EXAMPLES

General

The reactions in the hydrocarbon conversion Examples below were carried out in a stainless steel reactor of plug-flow design. Reactants were mixed and then fed into a preheater packed with inert Denstone packing and passed into a ½-inch O.D.×5-inch reactor tube filled with a 3–5 g catalyst composition charge. The entire reactor and preheater assembly was supported in a fluidized sand bath maintained at reaction temperature. Product was collected in a cooled vessel as it dripped from the reactor and analyzed by gas chromatography on a 60-meter fused silica capillary column. All hydrocarbon isomer amounts are given in percents by weight. In the case of use of mixed xylenes as feed, the xylenes contain about 20% ethylbenzene, the reaction products of which are not included in the data for the table below.

All reaction runs were at ambient pressure and 4–6 hours in length and the system was lined out for at least an hour before collecting conversion and selectivity data. These runs were made with ethylene by feeding 0.21 ml/min of aromatic compound together with 5.5 ml/min of ethylene (an 8:1 molar aromatic/ethylene ratio), or in the case of the ethanol runs, feeding a 8:1 molar aromatic/ethanol liquid mixture to the preheater from the feed reservoir. Each run used a 3–5 g catalyst charge and, due to variations in catalyst density, the WHSV are not always constant so that the % conversion values are not strictly comparable.

EXAMPLE 1

A 14.76 g portion of manganese acetate and a 29.45 g portion of boric acid were dissolved in 1000 ml of water. A 23.96 g portion of tetrapropylammonium bromide was dissolved in the solution and the pH raised to 9.8 with 35.05 g of ethylenediamine. Ludox AS-40 supplied by E. I. DuPont in the amount of 300.94 g was then added. The resulting mixture was stirred at room temperature for 15 minutes before recording the final pH and charging to a stainless steel autoclave. Digestion in the autoclave was allowed to proceed at 150° C. for a minimum of 3 days. The result was cooled, filtered, washed well with distilled water, and dried at 165° C. for 4 hours. The dried material was then calcined at 500° C. for 12 hours. The resulting solid was exchanged twice with ammonium acetate solutions and dried at 165° C. The product contained 2.09% by weight manganese.

EXAMPLE 2

A 17.77 g portion of nickel nitrate and a 24.73 g portion of boric acid were dissolved in 1000 ml of water. A 23.98 g portion of tetrapropylammonium bromide was dissolved in the solution and the pH raised to 9.5 with 24.74 g of ethylenediamine. Ludox AS-40 supplied by E. I. DuPont in the amount of 300.94 g was then added. The resulting mixture was stirred at room temperature for 15 minutes before recording the final pH and charging to a stainless steel autoclave. Digestion in the autoclave was allowed to proceed at 150° C. for a minimum of 3 days. The result was cooled, filtered, washed well with distilled water, and then dried at 165° C. for 4 hours. The dried material was then calcined at 500° C. for 12 hours. The resulting solid was exchanged twice with ammonium acetate solutions and dried at 165° C. The product contained 0.91% by weight nickel.

EXAMPLE 3

A 15.42 g portion of cobalt nitrate and a 24.55 g portion of boric acid were dissolved in 1000 ml of water. A 40.55 g portion of tetrapropylammonium bromide was dissolved in the solution and the pH raised to 9.9 with 40.41 g of ethylenediamine. Ludox AS-40 supplied by E. I. DuPont in the amount of 300.94 g was then added. The resulting mixture was stirred at room temperature for 15 minutes before recording the final pH and charging to a stainless steel autoclave. Digestion in the autoclave was allowed to proceed at 150° C. for a minimum of 3 days. The result was cooled, filtered, washed well with distilled water, and then dried at 165° C. for 4 hours. The dried material was then calcined at 500° C. for 12 hours. The resulting solid was exchanged twice with ammonium acetate solutions and dried at 165° C. The product contained 1.01% by weight cobalt. Surface analysis of this sieve using XPS indicates that the cobalt is present in the +2 oxidation state and the Co(II) is incorporated in the sieve lattice rather than present as CoO.

The powder diffraction X-ray pattern is shown in the Table below.

TABLE I

| Interplanar Spacing d, Å | $I/I_o$, % |
|---|---|
| 11.18 | 100 |
| 10.03 | 49 |
| 3.84 | 47 |
| 3.81 | 35 |
| 3.71 | 23 |
| 9.75 | 17 |
| 3.63 | 16 |
| 3.74 | 14 |
| 5.98 | 14 |
| 6.35 | 11 |
| 5.56 | 9 |
| 5.70 | 8 |
| 4.25 | 7 |

TABLE I-continued

| Interplanar Spacing d, Å | I/Io, % |
| --- | --- |
| 6.70 | 5 |
| 3.43 | 5 |
| 2.98 | 5 |
| 4.97 | 5 |
| 3.04 | 4 |
| 3.30 | 4 |
| 2.96 | 4 |
| 4.35 | 4 |
| 1.98 | 4 |
| 2.00 | 4 |
| 4.60 | 4 |
| 5.01 | 4 |
| 2.93 | 3 |
| 3.99 | 3 |
| 5.35 | 2 |
| 3.34 | 2 |
| 3.47 | 2 |
| 2.48 | 2 |
| 2.72 | 2 |
| 2.60 | 2 |
| 3.13 | 2 |
| 3.23 | 1 |
| 2.39 | 1 |
| 1.86 | 1 |
| 2.50 | 1 |
| 7.42 | 1 |
| 1.45 | 1 |
| 1.90 | 1 |
| 1.94 | 1 |
| 2.40 | 1 |
| 10.68 | 1 |
| 1.44 | 1 |
| 2.58 | 1 |
| 1.66 | 1 |
| 5.12 | 1 |
| 4.44 | 1 |
| 3.39 | 1 |
| 1.65 | 1 |
| 1.65 | 1 |
| 2.85 | 1 |
| 1.39 | 1 |

EXAMPLE 4

A 7.99 g portion of copper acetate and a 24.76 g portion of boric acid were dissolved in 1000 ml of water. A 23.96 g portion of tetrapropylammonium bromide was dissolved in the solution and the pH raised to 9.5 with 23.90 g of 30% ammonia. Ludox AS-40 supplied by E. I. DuPont in the amount of 300.94 g was then added. The resulting mixture was stirred at room temperature for 15 minutes before recording the final pH and charging to a stainless steel autoclave. Digestion in the autoclave was allowed to proceed at 150° C. for a minimum of 3 days. The result was cooled, filtered, washed well with distilled water, and then dried at 165° C. for 4 hours. The dried material was then calcined at 500° C. for 12 hours. The resulting solid was exchanged twice with ammonium acetate solutions and dried at 165° C. The product contained 0.46% by weight copper.

EXAMPLE 5

A 7.51 g portion of zinc acetate and a 20.80 g portion of boric acid were dissolved in 1000 ml of water. A 23.96 g portion of tetrapropylammonium bromide was dissolved in the solution and the pH raised to 10.2 with 33.98 g of ethylenediamine. Ludox AS-40 supplied by E. I. DuPont in the amount of 300.94 g was then added. The resulting mixture was stirred at room temperature for 15 minutes before recording the final pH and charging to a stainless steel autoclave. Digestion in the autoclave was allowed to proceed at 150° C. for a minimum of 3 days. The result was cooled, filtered, washed well with distilled water, and then dried at 165° C. for 4 hours. The dried material was then calcined at 500° C. for 12 hours. The resulting solid was exchanged twice with ammonium acetate solutions and dried at 165° C. The product contained 0.69% by weight zinc.

EXAMPLE 6

A 10.00 g portion of ytterbium acetate and a 24.80 g portion of boric acid were dissolved in 1000 ml of water. A 23.96 g portion of tetrapropylammonium bromide was dissolved in the solution and the pH raised to 9.8 with 13.2 g of iminodiacetate and 31.0 g of 30% ammonia. Ludox AS-40 supplied by E. I. DuPont in the amount of 300.94 g was then added. The resulting mixture was stirred at room temperature for 15 minutes before recording the final pH and charging to a stainless steel autoclave. Digestion in the autoclave was allowed to proceed at 150° C. for a minimum of 3 days. The result was cooled, filtered, washed well with distilled water, and then dried at 165° C. for 4 hours. The dried material was then calcined at 500° C. for 12 hours. The resulting solid was exchanged twice with ammonium acetate solutions and dried at 165° C. The product contained 1.31% by weight ytterbium.

EXAMPLE 7

The molecular sieves of Examples 1-6 were converted to catalyst compositions containing 40% by weight metalloborosilicate sieve and 60% by weight alumina as follows. A sample of sieve was mixed into a water sample to which was added a weight of PHF alumina, supplied by American Cyanamid, and the result blended for 3 minutes. This mixture was then gelled with concentrated (30%) ammonia and mixed in a mixmaster for 5 minutes. The result was dried at 365° C. for 4 hours, calcined at 500° C. for an additional 4 hours, and ground to 18/40 mesh. The amounts of sieve and reagents used are shown in the Table below.

TABLE II

| Metalloborosilicate | Sieve (g) | Water (g) | Alumina (g) | NH$_4$OH (ml) |
| --- | --- | --- | --- | --- |
| Mn | 31.67 | 105 | 462.3 | 45 |
| Ni | 20.05 | 40.6 | 304.7 | 31 |
| Co | 30.20 | 90 | 468.5 | 45 |
| Cu | 42.50 | 40 | 607 | 60 |
| Zn | 47.10 | 65.0 | 625.05 | 60 |
| Yb | 20.70 | 40.5 | 301.2 | 30 |

EXAMPLE 8

The copper metalloborosilicate of Example 4 matrixed as in Example 7 was impregnated with a phosphorus compound as follows: In a small beaker containing 30 ml of water and 3.5 g of the copper borosilicate was dissolved 11.7 g of NH$_4$H$_2$PO$_4$. The mixture was placed in a shaker bath at 50° C. overnight. The sample was dried at 130° C. overnight and calcined at 600° C. This impregnated catalyst composition contained approximately 9% phosphorus by weight.

EXAMPLE 9

The metalloborosilicates of Examples 1 through 6, matrixed as in Example 7 or matrixed and impregnated as in Example 8, were used to ethylate xylene or a mixed xylene as set out in General above. The conversion and selectivity results are given in the Table below.

TABLE III

Conversion of Xylene to Dimethylethylbenzenes

| Example[1] No. | Feed | Alkylating[3] Agent | Isomer Selectivity (%) | | | | | Reaction T(°C.) | C8 Conversion[2] (%) |
|---|---|---|---|---|---|---|---|---|---|
| | | | 3,5 | 2,5 | 2,4 | 3,4 | 2,6 | 2,3 | |
| 1 | Mixed C8 | A | 0.7 | 2.5 | 5.6 | 89.8 | — | 1.4 | 325 | 7.6 |
| 1 | Mixed C8 | B | 1.0 | 3.8 | 8.0 | 86.2 | — | 1.0 | 325 | 5.8 |
| 1 | p-xylene | A | 0.7 | 4.0 | 4.8 | 88.5 | 0.9 | 1.1 | 350 | 7.0 |
| 1 | o-xylene | A | 0.9 | 1.9 | 4.6 | 88.2 | — | 4.4 | 350 | 5.9 |
| 2 | Mixed C8 | A | 2.0 | 5.0 | 9.6 | 81.0 | — | 2.4 | 300 | 8.2 |
| 2 | Mixed C8 | B | 0.9 | 3.2 | 6.4 | 89.5 | — | — | 325 | 7.2 |
| 2 | o-xylene | A | 1.8 | 3.4 | 7.1 | 83.8 | — | 3.9 | 350 | 8.6 |
| 3 | Mixed C8 | A | (1) | 2.0 | 5.4 | 91.6 | — | 1.0 | 325 | 7.1 |
| 3 | Mixed C8 | B | — | 3.2 | 6.8 | 88.5 | — | 1.5 | 325 | 5.5 |
| 3 | o-xylene | A | — | 1.6 | 4.1 | 89.5 | — | 4.8 | 350 | 5.3 |
| 4 | Mixed C8 | A | 1.5 | 5.0 | 9.0 | 83.0 | — | 1.5 | 325 | 11.6 |
| 4 | Mixed C8 | A | — | 1.9 | 4.4 | 93.7 | — | — | 325 | 7.1 |
| 4 | Mixed C8 | B | 1.4 | 3.1 | 6.5 | 87.1 | — | 1.9 | 350 | 5.7 |
| 4 | p-xylene | A | 1.4 | 6.1 | 5.6 | 85.1 | — | 1.8 | 350 | 4.6 |
| 4 | o-xylene | A | — | 2.0 | 4.9 | 87.7 | — | 5.4 | | |
| 5 | Mixed C8 | A | 1.8 | 4.4 | 7.9 | 83.7 | — | 2.2 | 325 | 8.9 |
| 5 | Mixed C8 | B | 1.2 | 3.1 | 7.3 | 86.4 | — | 2.0 | 325 | 6.2 |
| 5 | o-xylene | A | 2.0 | 2.3 | 5.3 | 84.0 | — | 6.4 | 350 | 8.1 |
| 6 | Mixed C8 | B | — | 3.7 | 8.0 | 86.8 | — | 1.5 | 325 | 4.3 |
| 6 | p-xylene | A | 1.5 | 5.6 | 5.9 | 84.9 | — | 2.1 | 350 | 7.8 |
| 6 | o-xylene | A | 1.3 | 2.2 | 5.3. | 86.2 | — | 5.0 | 350 | 5.9 |
| 8 | Mixed C8 | A | — | 1.9 | 4.4 | 93.7 | — | — | 350 | 4.4 |
| Comparison[5] | Mixed C8 | A | 1.3 | 4.0 | 9.5 | 83.4 | — | 1.9 | 300 | 8.2 |
| Comparison[6] | Mixed C8 | A | 1.8 | 4.1 | 8.8 | 82.0 | — | 3.3 | 300 | 8.6 |
| Comparison[7] | Mixed C8 | A | 2.9 | 3.3 | 7.4 | 83.0 | — | 3.4 | 325 | 9.3 |
| Comparison[8] | Mixed C8 | A | 3.0 | 3.8 | 7.8 | 82.0 | — | 3.4 | 325 | 9.2 |

[1]Example No. refers to the molecular sieve used. Catalyst compositions used for the conversions were the sieves of Examples 1-6 matrixed as in Example 7.
[2]Out of a maximum of 12.5% based upon an 8:1 feed ratio, xylene to ethylating agent.
[3]Alkylating agent A is ethylene and alkylating agent B is ethanol
[4]Mixed C8 is a mixed xylene which was 19% o-xylene, 42% m-xylene, and 19% p-xylene.
[5]Sieve made according to Eur. Pat. Appl. No. 68796, Exs. 1-8, and supported 40% sieve and 60%-Al2O3.
[6]Sieve made according to the teachings of Eur. Pat. Appl. No. 68796, and supported 40% sieve and 60%-Al2O3.
[7]Catalyst composition of footnote 5 impregnated with manganese acetate and containing 2% by weight Mn.
[8]Catalyst composition of footnote 6 impregnated with cobalt acetate and containing 2% by weight Co.

What is claimed is:

1. A process comprising contacting xylene and an ethylating agent under hydrocarbon conversion conditions to selectively form 3,4-dimethylethylbenzene in the presence of a catalyst composition comprising a crystalline metalloborosilicate molecular sieve containing between about 0.1 weight percent of about 6 weight percent of metal ion selected from the group consisting of manganese, cobalt, nickel, copper, zinc, and ytterbium ions, composited in an inorganic matrix, said sieve made by crystallization from an aqueous solution containing ammonia or an organic base, an organic template compound, a metal ion-affording compound selected from soluble compounds of said metal ion, and sources of an oxide of silicon and boron and providing an X-ray pattern comprising the following X-ray diffraction lines and assigned strengths:

| Interplanar Spacing d, Å | Assigned Strength | Interplanar Spacing d, Å | Assigned Strength |
|---|---|---|---|
| 11.18 ± 0.20 | VS | 3.84 ± 0.10 | MS |
| 10.03 ± 0.20 | MS | 3.81 ± 0.10 | M |
| 9.75 ± 0.20 | W | 3.74 ± 0.10 | W |
| 6.35 ± 0.20 | W | 3.71 ± 0.10 | M |
| 5.98 ± 0.15 | W | 3.63 ± 0.10 | W |

2. The process of claim 1 wherein the amount of said metal ion in said sieve is between about 0.5 and about 4 weight percent.

3. The process of claim 1 wherein said metal ion-affording compound is selected from the group consisting of compounds of manganese, cobalt, nickel, and zinc.

4. The process of claim 2 wherein said metal ion-affording compound is selected from the group consisting of soluble compounds of manganese, cobalt, nickel, and zinc.

5. The process of claim 1 wherein said inorganic matrix is silica, silica-alumina, or alumina.

6. The process of claim 2 wherein said inorganic matrix is silica, silica-alumina, or alumina.

7. The process of claim 3 wherein said inorganic matrix is silica, silica-alumina, or alumina.

8. The process of claim 4 wherein said inorganic matrix is silica, silica-alumina, or alumina.

9. The process of claim 1 wherein said inorganic matrix is alumina.

10. The process of claim 2 wherein said inorganic matrix is alumina.

11. The process of claim 3 wherein said inorganic matrix is alumina.

12. The process of claim 4 wherein said inorganic matrix is alumina.

* * * * *